United States Patent [19]

Greenbaum

[11] Patent Number: 5,100,781
[45] Date of Patent: Mar. 31, 1992

[54] MEASUREMENT OF GAS PRODUCTION OF ALGAL CLONES

[75] Inventor: Elias Greenbaum, Oak Ridge, Tenn.

[73] Assignee: Gas Research Institute, Chicago, Ill.

[21] Appl. No.: 863,193

[22] Filed: May 14, 1986

[51] Int. Cl.$^5$ .................... C12Q 1/04; C12Q 1/02; C12M 1/04
[52] U.S. Cl. .............................. 435/34; 435/29; 435/39; 435/257; 435/287; 435/291; 435/313; 435/946; 435/807
[58] Field of Search ............... 435/807, 29, 313, 287, 435/291, 309, 946, 257, 173, 34, 39; 436/181

[56] References Cited
U.S. PATENT DOCUMENTS 4,401,755  8/1983  Weaver .................................. 435/34
4,647,531  3/1987  Kamentsky ............................. 435/7

Primary Examiner—Esther L. Kepplinger
Assistant Examiner—Toni R. Scheiner
Attorney, Agent, or Firm—Speckman & Pauley

[57] ABSTRACT

A rapid, non-destructive process for screening individual photosynthetic clonal colonies for selected gas producing capacity. Gas produced upon illumination of discrete algal clonal colonies grown on solid growth medium is continuously swept away in a carrier gas stream and conveyed to gas detectors for analysis. Hydrogen producing algal clones with enhanced gas production capacities and sustained production may be identified.

19 Claims, 1 Drawing Sheet

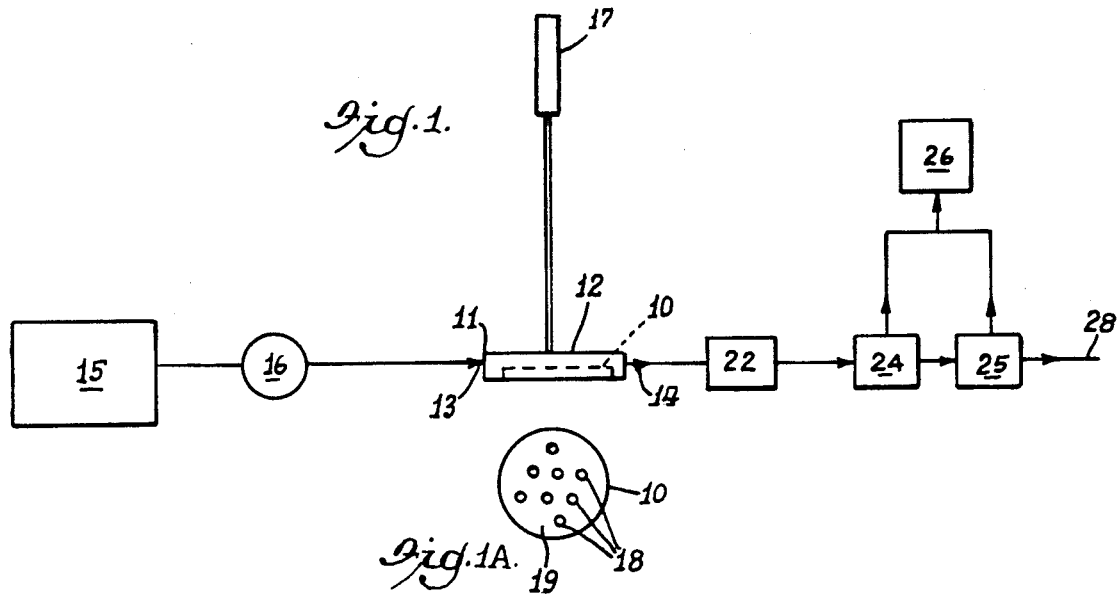
Fig. 1.
Fig. 1A.
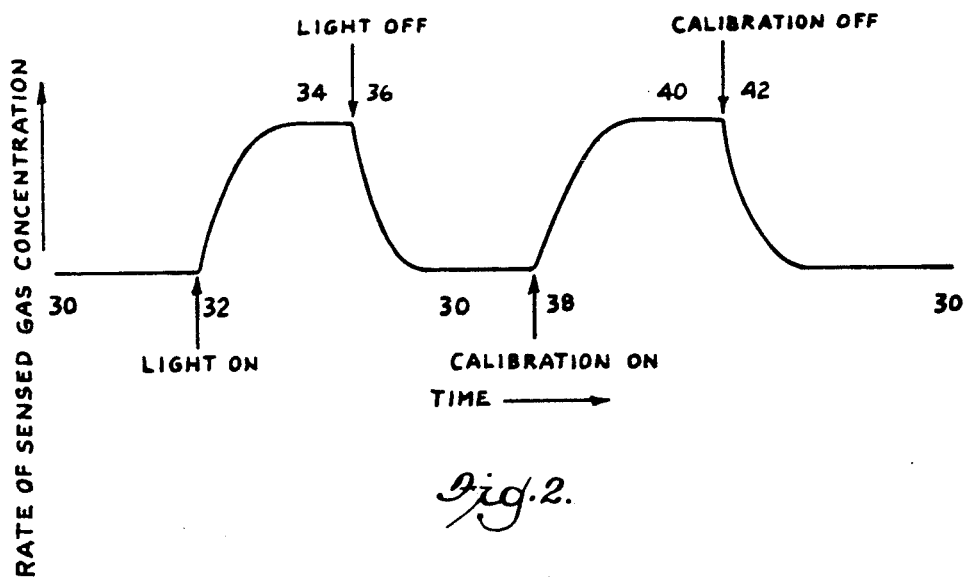
Fig. 2.

MEASUREMENT OF GAS PRODUCTION OF ALGAL CLONES

BACKGROUND OF THE INVENTION

1. Field of the Invention

The present invention relates generally to a rapid screening process for measuring selected gas production of photosynthetic algal clones, and relates more specifically to a method for screening individual photosynthetic algal clones for gaseous fuel production capacity by illuminating individual algal colonies grown on a solid growth medium and measuring selected gases produced therefrom.

2. Description of the Prior Art

It is well known that certain species of algae cultivated under anaerobic conditions are capable of hydrogen photoproduction. The gas producing capabilities and anaerobic metabolism of Scenedesmus unicellular algae and other species, for example, have been investigated. (See H. Gaffron and J. Rubin, "Fermentative and Photochemical Production of Hydrogen in Algae", *J. Gen. Physiol.*, 219-240 (1942) and J. J. Brand, "Survey of Hydrogenase Activity in Algae", Final Report for Subcontract No. B-1-9229-1 under Prime Contract No. EG-77-C-01-4042, University of Texas at Austin) Different algal species, and different strains of the same species exhibit varying degrees of hydrogen photoproduction, or none at all, and past efforts to measure photoproduction of different algal species and strains have been cumbersome and time consuming. Quantification of hydrogen production is important, since algal photoproduction represents potential for gaseous fuel production from renewable inorganic resources.

One common method for screening algae to determine their hydrogen producing capabilities involves growing algae in a liquid culture medium and measuring the hydrogen evolved with a reverse-biased Clark-type oxygen electrode. This method is described in R. Wang, F. P. Healy and J. Myers, "Amperometric Measurement of Hydrogen Evolution in Chlamydomonas", *Plant Physiol.* 48, 108-110 (1970) and R. T. Wang, "Amperometric Hydrogen Electrode", in *"Methods in Enzymology"* 69, 409-413 (1980), Academic Press. According to this screening method, the algae cultured in liquid medium are grown in a culture vessel, and hydrogen and oxygen gas produced by an appropriate aliquot of the algae are confined to a static volume. As hydrogen and oxygen gas concentrations increase, algal photoproduction is inhibited and hydrogenase activity is reduced. This inhibitory effect varies with individual algal strains, and therefore cannot be quantified generally. Calibration of the reverse-biased Clark electrode is difficult and measurements of hydrogen produced are often inaccurate due to the electrochemical instability of the reverse-biased Clark electrode.

U.S. Pat. No. 4,442,211 teaches a method for measuring hydrogen production of algae cultured in an aqueous phase. Algae grown in a liquid culture medium are sequentially subjected to anaerobic conditions, aerobic conditions, and then anaerobic conditions again to provide an enhanced rate of hydrogen and oxygen gas production. Hydrogen and oxygen gas production are measured by illuminating the cell culture in an anaerobic environment, passing an inert gas over the culture as a carrier for removing the hydrogen and oxygen gases produced, and then determining product gas composition by means of hydrogen and oxygen gas sensors. One drawback of this screening method is that the entire volume of the liquid culture is irradiated to measure the collective gas production of all cells in the culture and the gas production of individual cells and strains within the culture volume cannot be determined. For example, mutant cells may have developed with greatly enhanced hydrogen producing capabilities, but the presence of these cells is not detectable since the gaseous production of the bulk culture volume is measured. This screening method is also limited from the standpoint that pure algal cultures must be maintained to determine the gas production capacity of different strains and species, and pure cell cultures are difficult to isolate and maintain.

U.S. Pat. No. 4,010,076 teaches hydrogen production by stabilized photometabolically active microbes grown on a support medium such as agar gel wherein an aqueous substrate solution flows through the reactor under anaerobic conditions in the presence of light and hydrogen gas produced is passed to a collection vessel. According to the teachings of this patent, microorganisms are immobilized on a solid support to facilitate separation of the gaseous product from the microorganisms.

Hydrogen photoproduction of algal cultures is dependent upon cellular hydrogenase activity, and measurement of hydrogenase levels in algal strains and species would, therefore, give some indication of hydrogen production capacity. Enzymatic assays, however, typically require destruction of the living cells and are very time consuming. A colony screening method for isolation of hydrogenase regulatory bacterial mutants wherein bacterial colonies are grown on a solid agar medium and transferred to filter paper discs for screening is taught in H. G. Schlegel and M. Meyer, "Isolation of Hydrogenase Regulatory Mutants of Hydrogen-Oxidizing Bacteria by a Colony-Screening Method", *Arch. Microbiol.* 141, 377-383 (1985). Detection of hydrogenases in bacterial colonies transferred to filter paper discs is determined by soaking the discs in a dye solution and exposing them to hydrogen gas. Dye reduction indicates the presence of hydrogenase containing colonies.

SUMMARY OF THE INVENTION

It is an object of the present invention to provide a method which allows rapid, non-destructive screening of individual algal clonal colonies for selected gas producing capabilities.

It is yet another object of the present invention to provide accurate quantitation of selected gas production of algal clonal colonies.

It is yet another object of the present invention to provide a method allowing long term, steady state monitoring of gas production by algal clonal colonies.

It is yet another object of the present invention to provide a method which permits rapid, highly automated screening of discrete algal clonal colonies for photosynthetic gas production capabilities.

According to the process of the present invention, pure algal colonies are isolated and grown on a solid growth medium, such as an agar gel containing medium Microbiological methods for isolating pure cell cultures are well known, and suitable methods are taught by G. J. Tortora, B. R. Funke, and C. L. Case, *Microbiology*, Benjamin/Cummings Publishing Co., Menlo Park, Calif. (1982), pp. 156-157. In general, a dilute inoculum of microorganisms is spread on the surface of solid growth medium so that individual cells are sparsely distributed and well isolated, and discrete clonal colonies are obtained. The cell cultures are then grown in a controlled environment until desired colony sizes are obtained. Each discrete cell colony is a clonal colony, and the gas production of each algal clone may thus be measured.

For measurement of selected gas production, a cell culture plate with suitably sized clonal colonies is placed in a chamber hermetically sealed from the external atmosphere provided with inlet and outlet ports for carrier gas flow and at least one light transmitting window allowing illumination of individual colonies. An inert compressed gas which is unreactive with and different from the gases to be measured, and inert with respect to the algal colonies and the support matrix is used as a carrier gas. The carrier gas is humidified prior to introduction into the sealed chamber to prevent desiccation of the algal colonies.

A light source, and preferably a collimated light source such as a laser beam, is provided outside the sealed chamber to direct a focused or collimated light beam on individual cell colonies. The light source and/or the cell culture dish are movable with respect to one another to provide sequential illumination of each discrete clonal colony through the light transmitting window of the sealed measurement chamber for selected gas production measurement. As each discrete colony is irradiated, photosynthesis commences and gaseous products, such as molecular hydrogen and oxygen, are evolved. Product gases are continuously transported out of the sealed chamber by the carrier gas, and conveyed to volatile product detectors such as gas sensors for selected gas measurement. Gas sensor means continuously monitor the concentration of the selected gases, such as molecular hydrogen and/or oxygen gases in the product stream.

According to this process, the gas production capability of discrete algal clonal colonies may be determined quickly and accurately and without any deleterious effects on the cell cultures. Discrete algal clones with desirable gas producing characteristics may be identified, separated, studied and/or grown in larger quantities as desired according to the process of the present invention.

BRIEF DESCRIPTION OF THE DRAWINGS

The above mentioned and other features of the present invention, and the manner of obtaining them, will become apparent and the invention will be best understood by reference to the following description of preferred embodiments read in conjunction with the accompanying drawings, in which:

FIG. 1 shows a highly schematic representation of an apparatus for use in the process of the present invention;

FIG. 1A shows a top view of a culture dish with discrete colonies; and

FIG. 2 shows a graph illustrating one aspect of the process of the present invention.

DESCRIPTION OF THE PREFERRED EMBODIMENTS

The process of the present invention is suitable for measuring selected gas production of discrete microbial colonies, and is especially suitable for measuring hydrogen photoproduction of discrete algal clonal colonies cultured on solid growth medium. Suitable growth media for many different types of microbial organisms are well known to the art, and growth media may be adjusted to accommodate the requirements of different microbial populations, as is known to the art. The following culture medium is suitable for the growth of many algal colonies:

| Per liter: | |
|---|---|
| Culture Medium | |
| Beijerinck's solution | 30 ml |
| Phosphate solution | 50 ml |
| Trace elements solution | 1 ml |
| $H_2O$ | 899 ml |
| Beijerinck's Solution | |
| $NH_4Cl$ | 8.0 gm |
| $CaCl_2.2H_2O$ | 1.0 gm |
| $MgSO_4.7H_2O$ | 2.0 gm |
| $H_2O$ | to 1 liter |
| Phoshate Solution | |
| $K_2HPO_4$ | 14.34 gm |
| $KH_2PO_4$ | 7.26 gm |
| $H_2O$ | to 1 liter |
| Trace Elements Solutions | |
| EDTA, disodium salt | 50.0 gm |
| $ZnSO_4.7H_2O$ | 22.0 gm |
| $H_3BO_4$ | 11.4 gm |
| $MnCl_2.4H_2O$ | 5.06 gm |
| $FeSO_4.7H_2O$ | 4.99 gm |
| $CoCl_2.6H_2O$ | 1.61 gm |
| $CuSO_4.5H_2O$ | 1.57 gm |
| $(NH_4)_6Mo_7O_{24}.4H_2O$ | 1.10 gm |
| $H_2O$ | to 1 liter |

In addition, 1.5 wt. percent agar, or a similar solidifying agent, is added to the defined culture medium to provide a solid growth matrix.

According to a preferred embodiment, about 1 wt. percent, based upon the weight of the growth medium, ion-equilibrated charcoal powder is added to the growth medium. Ion-equilibrated charcoal powder may be prepared by exchanging potential charcoal ion-exchange sites with available liquid culture medium ions and then separating the powder from the liquid. The charcoal powder is provided in the solid growth matrix to reduce light scatter and stray illumination and to prevent the light source, when it is directed at a discrete algal colony, from inducing photosynthetic activity in surrounding algal colonies.

Cell cultures of clonal algal colonies are preferably prepared from a dilute, mixed culture inoculum of algae spread on the surface of the solidified growth medium as is well known to the art. The solid growth medium may be provided on a petri dish, or on other types of cell culture dishes. Cell cultures are then placed in a conventional facility for growing algae under controlled conditions of temperature, humidity and atmospheric conditions, such as an incubator or the like. Suitable growth conditions are well known to the art. The cell cultures are grown until discrete colonies are visible, and preferably until discrete colonies have reached a diameter of about 1 to 4 mm, and most preferably about 2 mm.

According to the process of the present invention and utilizing the means schematically shown in FIG. 1, carrier gas supply means 15 provides a pressurized, inert carrier gas which is unreactive with and different from gases produced by the algal clonal colonies. Nitrogen, helium and argon comprise preferred carrier gases, but other inert gases are also suitable. Carrier gas is passed through humidifier means 16, which humidifies the carrier gas to the extent necessary to prevent desiccation of the algal clonal colonies. Humidified carrier gas is introduced into measurement chamber 11 hermetically sealed from the external atmosphere, in which culture dish 10 with discrete algal clonal colonies 18 supported on solid growth medium has been placed. Hermetically sealed measurement chamber 11 has inlet 13 and outlet 14 ports to provide carrier gas flow and light transmitting window 12 on at least one side to permit illumination of individual algal colonies 18.

Light source 17 provides illumination of discrete algal colonies 18 through light transmitting window 12 of sealed measurement chamber 11. Discrete algal clonal colonies 18 are individually irradiated by light source 17 to initiate photosynthetic activity and gas production. Light source 17 may comprise any light source capable of providing focused or collimated light at a wavelength which induces photoproduction of gases by an algal colony. Light sources providing light at wavelengths from about 400 nm to about 700 nm and capable of focusing on an individual cell colony are suitable. Light source 17 preferably comprises a collimated light source, such as a laser beam, and suitable collimated light sources, such as a helium-neon laser, argon-ion laser and ruby laser are known to the art. Light source 17 is directed at and/or focused on individual colonies and is preferably aligned above and directed generally perpendicular to the plane defined by solid growth medium 19, or in any other orientation to reduce light scatter and stray illumination and to prevent induction of photosynthetic activity in surrounding colonies. The light beam provided by light source 17 is preferably of about the same diameter as the cell colony it illuminates at the point where the light beam is incident on the discrete clonal colony. Light source 17 and culture dish 10 are movable laterally with respect to one another to provide sequential focusing of light source 17 on each discrete algal clonal colony on culture dish 10. Light source 17 may be adjustable in a plane generally parallel to the plane of solid growth medium in culture dish 10, or culture dish 10 and/or measurement chamber 11 may be adjustable with respect to light source 17.

Gases evolved as a result of photosynthetic activity are continuously transported by humidified carrier gas from sealed measurement chamber 11 to volatile product detectors, such as gas sensors 24 and 25. One or more gas sensors may be provided according to the process of the present invention. One suitable gas sensor for hydrogen gas detection is a Figaro TGS No. 812 combustible gas sensor that has been calibrated using Faraday's Law of Electrochemical Equivalence. Other types of gas sensors suitable for detection of hydrogen and other selected gases, such as oxygen, are well known to the art.

Calibration cell 22 is provided to calibrate and/or monitor the performance of gas sensors 24 and 25. If hydrogen is the selected gas for measurement, calibration cell 22 preferably comprises an electrolysis cell. By electrolyzing water in an electrolysis cell with a measured current, a known amount of hydrogen and oxygen would be introduced in the stream of carrier gas in accordance with Faraday's law of electrochemical equivalence. Alternatively, gases of any composition may be calibrated using calibrated leak cells that are available commercially. During illumination of an individual colony, one or more gas sensors 24, 25 continuously monitor the concentration and/or quantity of selected gases in the carrier gas stream. Sensor measurements obtained during illumination of cell colonies and calibration may be processed, stored and/or recorded by data processing device 26. Data processing device 26 may comprise a microcomputer providing more detailed analysis of the selected gas measurements for discrete algal clones.

Carrier gas supply means 15, humidifier 16, sealed measurement chamber 11, calibration cell 22 and gas sensors 24 and 25 are provided in gas-tight communication with one another as shown in FIG. 1. The apparatus may be vented to the atmosphere by vent 28.

In operation, when algal clonal colonies have grown to a desired colony size, preferably about 2 mm in diameter, gas production measurements are commenced. Culture dish 10 is placed in sealed gas measurement chamber 11 and humidified carrier gas is passed therethrough to determine system baseline gas concentration 30 as shown in FIG. 2. For example, if hydrogen production is the desired gas measurement, a hydrogen gas concentration baseline is established prior to illumination. An oxygen gas concentration baseline may also be established to measure hydrogen and oxygen gas production simultaneously upon illumination. After system baseline gas concentrations 30 have been established, light source 17 is activated to illuminate an individual discrete algal clonal colony, as shown at point 32 in FIG. 2. If the colony does produce the selected gas in response to illumination, the measured relative gas concentration increases, shown as the curve between points 32 and 34, until a steady-state measured gas concentration is reached. Illumination and gas measurement may be continued if sustained gas production capabilities are of interest. After measurement of the desired gas production, light source 17 is inactivated at point 36 and the selected gas concentration is permitted to return to baseline gas concentration 30. After a steady state baseline gas concentration 30 has been established, calibration cell 22 is activated, as shown at point 38, and the calibration gas concentration increases, shown as the curve between points 38 and 40, until a steady state calibration gas concentration is reached. Calibration cell 22 is inactivated at point 42 and the calibration gas concentration is permitted to return to baseline gas concentration 30. Illumination of another individual discrete algal clonal colony may then be commenced for gas production measurements, and the cycle as shown in FIG. 2 is repeated. In this fashion, discrete algal clonal colonies may be rapidly screened for gas production capabilities, and accurate quantification of selected gas production is provided. The calibration curve may be run after the gas production measurement of each clonal colony, or a series of gas production measurements may be run sequentially, with the calibration run after each series of measurements.

The process of the present invention is not limited to measuring the hydrogen photoproduction of individual algal clonal colonies, although it is especially suitable for this purpose. Any desired gas production may be measured with a suitable gas detector, and the gas production capacity of any cells which produce gas upon illumination may be measured according to the process of the present invention.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein may be varied considerably without departing from the basic principles of the invention.

I claim:

1. A process for screening a plurality of discrete individual cell colonies for photosynthetic selected gas producing capabilities, comprising:

culturing a plurality of discrete, clonal cell colonies on a solidified growth medium in a cell culture dish;

placing said cell culture dish in a gas measurement chamber sealed from external atmosphere and having at least one light transmitting window;

separately illuminating a single said discrete clonal cell colony by means of a light source penetrating said light transmitting window focused or collimated upon said single discrete clonal cell colony thereby initiating gas photoproduction by said single discrete clonal cell colony, photoproduced gas passing to said gas measurement chamber;

passing an inert carrier gas stream through said gas measurement chamber flushing said photoproduced gas therefrom into at least one product gas detector; and measuring at least one selected gas concentration in said carrier gas stream comprising said photoproduced gas by means of said product gas detector.

2. A process according to claim 1 wherein said discrete, clonal cell colonies comprise algal clonal colonies and said selected gas concentration measured is hydrogen gas concentration.

3. A process according to claim 1 wherein said discrete, clonal cell colonies comprise algal clonal colonies and hydrogen gas concentration and oxygen gas concentration are measured.

4. A process according to claim 1 additionally comprising recording at least one said selected gas concentration over time during said process for screening by a data processing means.

5. A process according to claim 4 additionally comprising analyzing at least one said selected gas concentration measurement over time in a microcomputer.

6. A process according to claim 1 additionally comprising measuring an absolute quantity of at least one said selected gas generated over time during said illumination of said single discrete clonal cell colony.

7. A process according to claim 1 additionally comprising continuously monitoring said selected gas concentration, determining a baseline selected gas concentration prior to illuminating said single discrete clonal cell colony, measuring at least one said selected gas concentration relative to said baseline selected gas concentration upon said illumination of said discrete clonal cell colony until a steady-state selected gas concentration is attained, and inactivating said light source after said steady-state selected gas concentration is attained until said baseline selected gas concentration is re-established.

8. A process according to claim 7 additionally comprising passing a calibration gas to said carrier gas stream after said baseline selected gas concentration is re-established, measuring at least one calibration gas concentration corresponding to said selected gas concentration until a steady-state calibration gas concentration is achieved, and stopping the flow of said calibration gas after said steady-state calibration gas concentration is achieved.

9. A process according to claim 8 wherein passing said calibration gas is performed to measure at least one said calibration gas concentration after measuring at least one said selected gas concentration for each said discrete clonal cell colony.

10. A process according to claim 8 wherein passing said calibration gas is performed to measure at least one said calibration gas concentration after measuring at least one said selected gas concentration for a plurality of said discrete cell colonies sequentially.

11. A process according to claim 1 wherein said solidified growth medium comprises ion-equilibrated charcoal powder in an amount sufficient to prevent stray illumination and reduce light scatter during illumination of said single discrete clonal cell colony.

12. A process according to claim 1 wherein said carrier gas is selected from the group consisting of: nitrogen, helium and argon.

13. A process according to claim 1 wherein said illumination is commenced when each said single discrete clonal cell colony is from about 1 mm to about 4 mm in diameter.

14. A process according to claim 1 wherein said light source provides light at wavelengths of about 400 nm to about 700 nm.

15. A process according to claim 1 wherein said light source comprises a collimated light source.

16. A process according to claim 15 wherein said collimated light source is directed in a plane perpendicular to the plane of said solid growth medium.

17. A process according to claim 15 wherein said collimated light source is selected from the group consisting of: a helium-neon laser, an argon-ion laser and a ruby laser.

18. A process according to claim 1 wherein said inert carrier gas stream is humidified to an extent necessary to prevent desiccation of said clonal cell colonies.

19. A process according to claim 1 wherein said light source and said cell culture dish are movable with respect to one another to provide said light to each said single discrete clonal cell colony.

* * * * *